US00PP11737P2

(12) United States Plant Patent
Berry

(10) Patent No.: US PP11,737 P2
(45) Date of Patent: Jan. 9, 2001

(54) TERNSTROEMIA PLANT NAMED 'CONTHERANN'

(75) Inventor: James Bryan Berry, Daphne, AL (US)

(73) Assignee: Plant Development Services Inc., Loxley, AL (US)

( * ) Notice: Under 35 U.S.C. 154(b), the term of this patent shall be extended for 0 days.

(21) Appl. No.: 09/027,475

(22) Filed: Feb. 20, 1998

(51) Int. Cl.[7] ..... A01H 5/00
(52) U.S. Cl. ..... Plt./226
(58) Field of Search ..... Plt./226

(56) References Cited

U.S. PATENT DOCUMENTS

P.P. 10,521 * 7/1998 Hunt et al. .

* cited by examiner

*Primary Examiner*—Howard J. Locker
*Assistant Examiner*—Wendy A Baker

(57) ABSTRACT

A new and distinct *Ternstroemia gymnanthera* plant found as an openly pollinated seedling. The new variety consistently produces a very high concentration of anthocyanin in new growth as well as a more uniform, upright growth habit and mature foliage color compared with other commercial varieties in the market class.

1 Drawing Sheet

BACKGROUND OF THE INVENTION

This new Ternstroemia variety was found as an openly pollinated seedling of *Ternstroemia gymnanthera,* maintained by Plant Development Services Inc. at County Road 68, Loxley, Ala. The seedling was found Oct. 15, 1992. The new and distinct *Ternstroemia gymnanthera* plant of this invention comprises a novel and valuable plant with a dense, upright, globose shape, and reddish-bronze new growth. The new growth of this plant is interestingly and clearly red due to anthocyanin which is of distinctly higher concentration than is typical of the species. The new variety has retained many of the outstanding attributes of its species, in particular its tolerance of insects and diseases which makes it adaptable to culture in the Sunbelt states. This plant is responsive to pruning and training, and may be employed in forming dense, attractive hedges, and maintained without an excessive amount of care. The upright habit of growth and the reddish new growth of this plant is similar to *Photinia*× *fraseri,* however, it is not susceptible to fungal leaf spot. Asexual propagation of the new plant by cuttings has been under Mr. Berry's direction at the same location. The increased number of plants were evaluated and demonstrated stability of the new characteristics from generation to generation. The plant cannot be reproduced true from seed.

SUMMARY OF THE INVENTION

The following are the most outstanding and distinguishing characteristics of this new cultivar when grown under normal horticultural practices in Loxley, Ala.

1. Moderate growth rate under normal fertilization and moisture conditions.

2. A uniformly dense, upright and globose growth habit 10–12' tall and 6–7' wide.

3. Easily trained into a small tree.

4. Attractive, very glossy foliage.

5. Good specimen plant.

6. The reddish/bronze color of the immature foliage is unique and offers a novel and strikingly appealing contrast of new foliage to old foliage in plants of this market class.

7. Hardy to Zone 7.

8. Performs well in sun or shade.

9. Resistant to fungal leaf spot.

10. Resistant to insect pests such as aphids and scales.

11. Very desirable in planters.

12. Makes a very good formal or informal hedge or screen.

13. Very good foundation plant for large buildings or corner plant for homes.

14. Has the ability to be sheared and trimmed to be kept within prescribed limits.

15. Easily propagated.

16. Withstands city conditions.

DESCRIPTION OF THE DRAWINGS

This new *Ternstroemia gymnanthera* variety is illustrated by the accompanying photographic prints in which.

Figure 1:
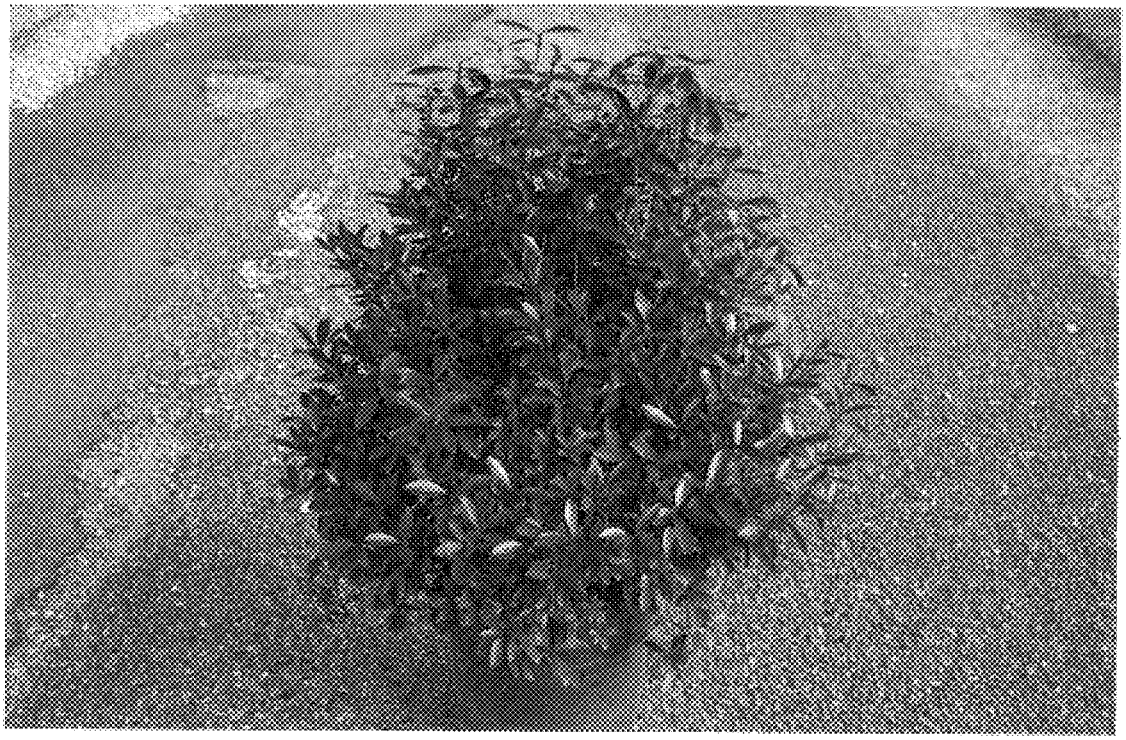
FIG. 1 shows the uniform growth habit and foliage color of the new plant.
Figure 2:
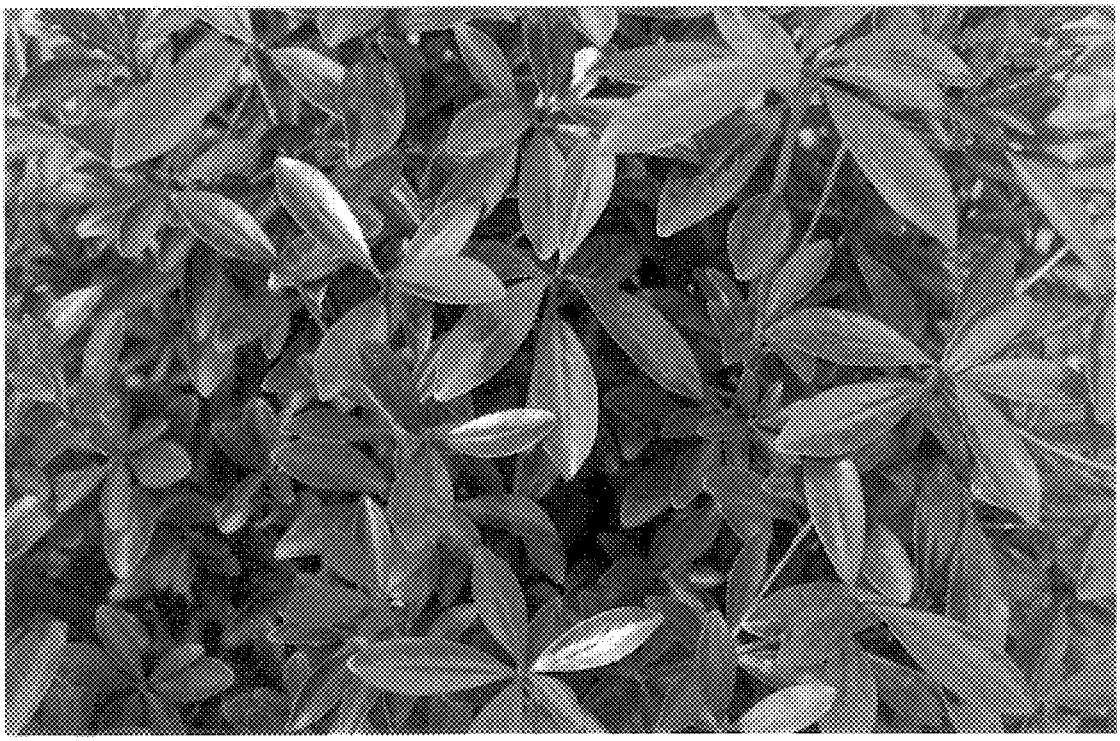
FIG. 2 shows a close-up view of the unusual reddish/bronze pigmentation of the leaves, petioles, and stems of the juvenile growth.

The colors shown are as true as is reasonably possible to obtain by conventional photographic procedures. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Ternstroemia based on my observations made of plants grown in wholesale commercial production practices, in greenhouses, and in established landscape plantings at Plant Development Services Inc. in Loxley, Ala.

Distinctive Characteristics:

| Characteristic | *Ternstroemia gymnanthera* (the species) | *Ternstroemia g.* '*Contherann*' |
|---|---|---|
| Height (Mature) | 8–10' | 10–12' |
| Width (Mature) | 6–8' | 6–7' |
| Leaf Length | 2½–4" | 2¼–3" |
| Leaf Width | ½–1½" | ¾–1⅛" |
| Leaf Shape | oblong to lanceolate | oblanceolate |
| Leaf Color (immature) | Yellow-Green Group 146A | Greyed-Red Group 178A |
| Leaf Color (mature) | Green Group 137A | Green Group 137A |

The seed parent of 'Contherann' is an un-named plant of Theaceae *Ternstroemia gymnanthera*. The genus name Ternstroemia was proposed by Jose Celestino Mutis (1732–1808) and first published by Carl von Linne (1741–1783). The original species name of this plant was *T. japonica,* named by Robert Wight (1796–1872) and George Arnott Walker-Arnott (1799–1868), however it was transferred to *T. gymnanthera* by Thomas Archibald Sprague (1877–1958).

There is confusion in the nursery trade in that what is called *Cleyera japonica* is actually *Ternstroemia gymnanthera.* Although similar, they differ in many ways. *Cleyera japonica* has a larger leaf 3–6" long and ¾–2" wide with an accuminate tip compared to 3–3½" long and ½–1½" wide with an obtuse tip. *Cleyera japonica* also has 25 stamens in one series unlike *Ternstroemia gymnanthera* which has more than 25 stamens in two or more series.

CLASSIFICATION

Botanic: *Ternstroemia gymnanthera* 'Contherann'.

Form: Upright, dense, and globose.

Size: In a period of four years from a rooted cutting the plant reaches a height of 4 to 5 feet and a spread of 3 to 4 feet. The plant normally grows at the rate of about 15 inches or more per year and reaches a height of 10–12 feet and a spread of 6–7 feet at maturity. A dense habit is maintained due to the abundant branch development.

Growh habit: Upright, dense, globose evergreen shrub. Moderate growth rate under normal fertilization and moisture conditions.

Foliage: Alternate, simple, evergreen, leathery, glabrous, narrowly oblanceolate, 2¼ to 3" long and ¾ to 1⅛" wide, bluntly pointed at the apex, base cuneate and margins are entire. The petioles are ⅛ to 3⁄16" long and Greyed-Purple Group 185B. The upper surface of the immature leaf is noticeably pigmented, Greyed-Red Group 178A, glossy and glabrous. The underside is Yellow-Green Group 146D and matte. The immature upper surface midribs are Greyed-Purple Group 185B and mature to Yellow Green Group 146C. The veins, other than the midrib, are generally not visible on the upper surface or the underside of the leaf. The leaf matures to Green Group 137A upper surface and Yellow-Green Group 146C on the underside. With the onset of cool weather in the fall, the immature foliage darkens to Greyed-Purple Group 187A and the mature foliage remains at Green Group 137A. There are occasional alternate foliaceous stipules which are ¼ to ½" long and 1⁄16 to ⅛" wide. The upper surface is Yellow-Green Group 144A and the underside is Yellow-Green Group 144B. The stipules are non-caducous.

In 1995, the date of initial spring growth was March 10, in Loxley, Ala. After the initial spring flush there was almost continuous growth until fall ending October 28, also in Loxley, Ala. This growth pattern was identical to that which is typical of the species. When grown in full sun, the internode length of this plant is ¼" to ⅝" which is typical of the species. When grown in light shade the internode length is ⅝" to 1¼" which is typical of the species. As would be expected, either plant grown in the shade results in a taller, less dense plant with larger leaves.

The average length of terminal growth of the initial spring flush is about 3 to 4" for a plant in full sun and about 4 to 5" when grown in shade. There are usually 4 to 6 flushes of growth under ideal growing conditions in Loxley, Ala. With each flush there is a 1 to 2½" stem which produces only foliaceous stipules. The true leaves are clustered at the end of each flush of growth with a whorled appearance. Very little trimming is needed to produce a dense 20" tall and 20" wide three gallon plant during the growing season. *Ternstroemia gymnanthera* seedlings grown under identical conditions were very inconsistent in vigor and color.

Although there are many variables involved, it should take about 8 to 10 years for this plant to reach a mature height of 10 to 12' and width of 6 to 7'. In the landscape little or no pruning is necessary to produce a dense, upright, and globose shrub in full sun. In shade, however, some trimming may be needed to produce the same effect.

Stems: The young shoots are Greyed-Purple Group 183A, glabrous, and matte. In about a month they change to Yellow-Green Group 144A and mature to Greyed-Green Group 197A. The mature stems are glabrous and rugose. The pith is solid and uniform.

Flowers: Axillary, solitary, bisexual, small, slightly fragrant, yellowish white and ½ to ¾" across. The inconspicuous flowers are produced from May to June on the previous year's wood or on short current season spurs. Buds are globular, Yellow-Green Group 145A, and without foliaceous appendages. Unbranched pedicels are ½ to ¾" long, curved near the end, and also Yellow-Green Group 145A. There are 5 sepals which are united at the base and 5 petals arranged regularly, united at the base, and imbricate in bud. There are 25 to 40 stamens in 2 to 3 series, and the anthers are glabrous, apiculate, and basifixed. As the flower opens the petals are Yellow-Green Group 145C and the pollen is Yellow Group 2D. The blooms last on the plant in the garden 3 to 6 days. A mature plant may have several hundred flowers.

Fruit: Indehiscent, berrylike, globose to ovoid, ½" diameter, 1" long; seeds usually 2–3 and Orange-Red Group 34A when mature. Immature fruit are Yellow-Green Group 146D maturing to Red Group 46B in late summer or early fall.

Culture: Grows well in a wide range of conditions and tolerates sun to shade. Grows in nearly any soil type, from moist to dry and sand to clay. Very heavy clays should be amended with peat moss, compost, or shredded pine bark to improve the soil texture. Poorly drained locations should be avoided. Responds well to mulching and medium applications of fertilizer; prefers ph 5 to 6.5. Very little pruning is needed, however, the plant can be sheared and maintained as a 3 to 5' shrub or pruned up into a small tree. Adaptable to containers and above ground planters. Propagated with semi-hardwood cuttings in late summer through the fall.

Pests: None serious.

I claim:

1. A new and unique variety of *Ternstroemia gymnanthera* plant named 'Contherann' as herein shown and described.

* * * * *